US008486353B2

(12) United States Patent
Wu et al.

(10) Patent No.: US 8,486,353 B2
(45) Date of Patent: *Jul. 16, 2013

(54) SAMPLE COLLECTION CUP WITH INTEGRATED ACTIVATABLE SAMPLE ANALYSIS SYSTEM

(75) Inventors: Yuzhang Wu, Hangzhou (CN); Lijiang Guo, Hangzhou (CN); Jeilin Dai, Hangzhou (CN); Hsiaoho Tung, San Diego, CA (US)

(73) Assignee: Alere Switzerland GmbH, Zug (CH)

( * ) Notice: Subject to any disclaimer, the term of this patent is extended or adjusted under 35 U.S.C. 154(b) by 1106 days.

This patent is subject to a terminal disclaimer.

(21) Appl. No.: 11/845,346

(22) Filed: Aug. 27, 2007
(Under 37 CFR 1.47)

(65) Prior Publication Data
US 2009/0031790 A1 Feb. 5, 2009

Related U.S. Application Data

(63) Continuation of application No. 11/433,043, filed on May 12, 2006, now abandoned, which is a continuation of application No. PCT/US2004/038429, filed on Nov. 15, 2004.

(60) Provisional application No. 60/519,907, filed on Nov. 14, 2003.

(51) Int. Cl.
*B01L 3/00* (2006.01)

(52) U.S. Cl.
USPC .......................................................... 422/557

(58) Field of Classification Search
USPC .......................................................... 422/557
See application file for complete search history.

(56) References Cited

U.S. PATENT DOCUMENTS

| 4,960,691 | A | * | 10/1990 | Gordon et al. | 435/6 |
| 5,022,411 | A | * | 6/1991 | Guirguis | 600/584 |
| 6,576,193 | B1 | | 6/2003 | Cui et al. | |
| 6,680,027 | B2 | * | 1/2004 | Kang et al. | 422/58 |
| 6,726,879 | B2 | * | 4/2004 | Ng et al. | 422/58 |

* cited by examiner

*Primary Examiner* — Lore Jarrett
(74) *Attorney, Agent, or Firm* — DLA Piper LLP (US)

(57) ABSTRACT

Medical and environmental diagnostic devices are described and claimed. Preferred embodiments feature cup (1) within cup configurations wherein one cup is dedicated, for the most part, to sample collection and another cup (2) is dedicated, for the most part, to assay performance. Communication between the cups is afforded by what is believed to be a unique valve assembly (3) and lid (7) tandem.

22 Claims, 4 Drawing Sheets

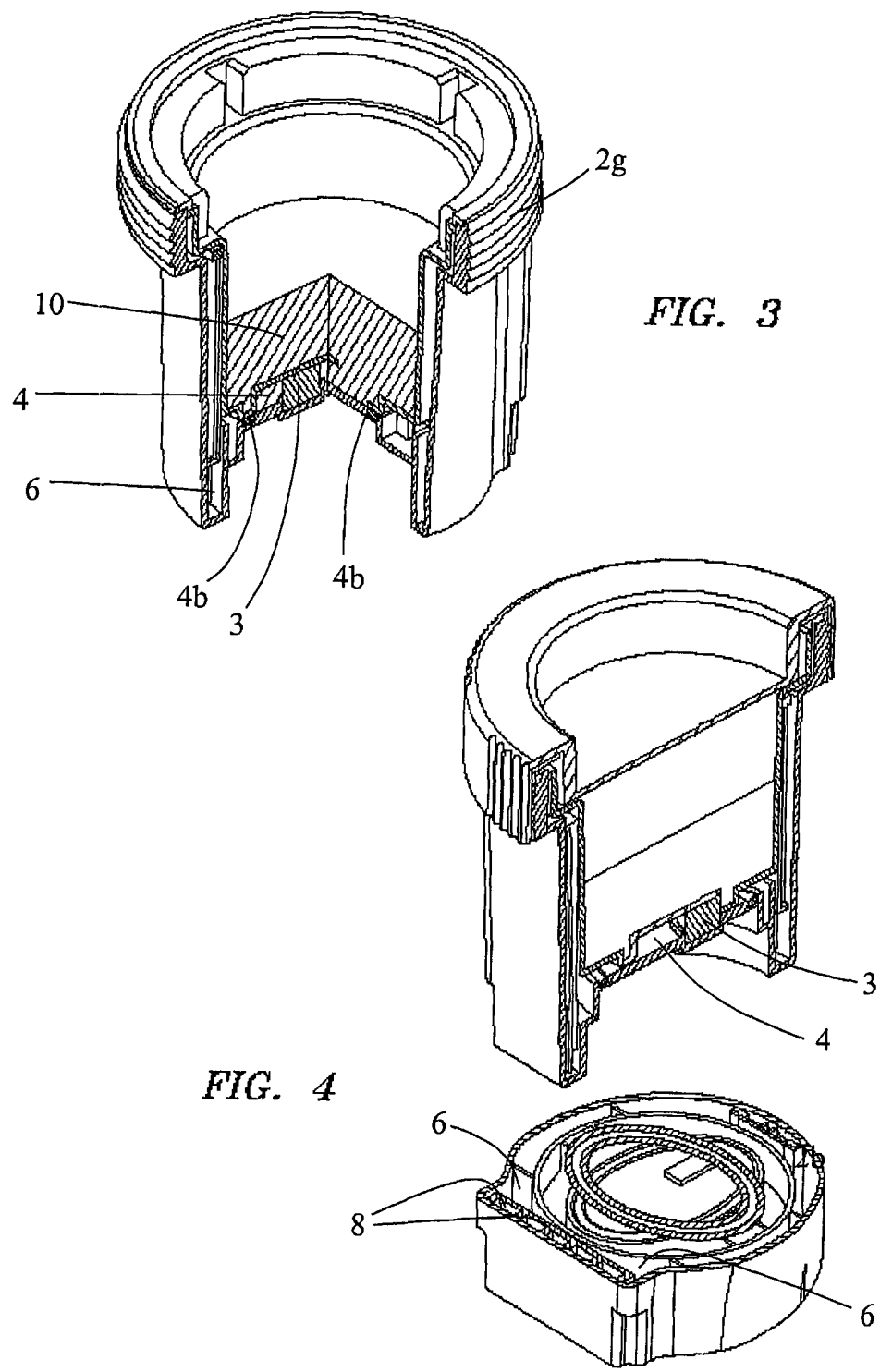

SAMPLE COLLECTION CUP WITH INTEGRATED ACTIVATABLE SAMPLE ANALYSIS SYSTEM

CROSS-REFERENCE TO RELATED APPLICATIONS

This application is a continuation of U.S. patent application Ser. No. 11/433,043, filed on May 12, 2006, which is abandoned; which is a continuation of PCT/US2004/038429, filed on Nov. 15, 2004; which claims priority to U.S. Provisional Application No. 60/519,907, filed Nov. 14, 2003, the contents of which are specifically incorporated herein.

FIELD OF THE INVENTION

The field of the invention relates to diagnostic devices for collecting and evaluating environmental or biological samples.

BACKGROUND OF THE INVENTION

The following Background of the Invention is intended to aid the reader in understanding the invention and is not admitted to be prior art.

There are a variety of medical and environmental diagnostic devices currently on the market. Most are designed to work in conjunction with a rapid analysis test device, such as a chemical or immunological test card. Some are used in clinical settings to test for indicators of health or disease. Others are used in nonclinical settings, such as by employment agencies, athletic commissions and prison facilities, to test for illicit drugs. Most if not all are complicated to use, requiring the technician to perform several steps to accomplish the analysis, or do not promote hygiene or the maintenance of sample purity. Most if not all existing devices simply are not designed to separate an aliquot of sample for testing, simultaneously preserving the remaining sample in an unadulterated state for confirmation or other testing at a later or earlier time.

SUMMARY OF THE INVENTION

The present invention provides a sample testing device and methods for use. In one embodiment the device is a urine cup for detecting the presence or amount of analytes in urine. In one embodiment the analyte is one or more drugs of abuse. In one embodiment the device is configured in a "cup within a cup" format, where a first cup is positioned or disposed within a second cup. Between the two cups is present one or more reservoirs. In one embodiment there is one reservoir present between the bottoms of the first and second cups, which is sealed at its base with an O-ring. A valve mechanism is present and regulates flow between the interior of the first cup and the reservoir(s). When a sample (e.g., urine) is added to the device, the sample flows from the interior of the first cup through an aperture therein and into one or more reservoirs or chambers between the cups, and remains in the reservoir due to the O-ring seal present at the base of the reservoir. When the first cup is moved from a first position into a second position, the reservoir seal is broken and sample is shunted from the reservoir or chamber through a passageway and into contact with a test element. Also, a valve member is actuated and seals the aperture so that no further sample is passed from the interior of the cup to the one or more reservoirs. The sample in the interior of the first cup is therefore preserved for confirmation testing.

In a first aspect the present invention provides a device for determining the presence or amount of an analyte in a sample. The device has a first cup which has an interior for holding a liquid sample, a top, one or more sidewalls, and a bottom. The device also contains a second cup having a top, one or more sidewalls, and a bottom. The first cup of the device is disposed within the second cup. The device also has at least one reservoir for containing an aliquot of sample which is located between the first and second cups, and the first cup has an aperture venting from the interior of the first cup into the at least one reservoir. The device also contains a valve assembly interfacing with the at least one reservoir for regulating communication of the aliquot of sample from the interior of the cup to the reservoir, and one or more test elements which have a sample application zone, and which are for determining the presence or amount of an analyte in the liquid sample. A passageway connects the at least one reservoir and the sample application zone.

The term "cup" as used in the claims is not limited to a particular geometric shape. Thus, the cup can have a square or oval shape, or any shape consistent with the function of the invention. Moreover, there is no requirement that the two cups need be of the same shape, although they certainly may be. The terms "top" and "bottom" also not limited to a particular geometric shape. A top may have a ledge, ridge, or lip, or the top may simply be the end of the upper portion of the cup. The "bottom" also may take a variety of shapes, such as flat, conical, or another shape consistent with its function as described herein. A "reservoir" refers to an volumetric area where an aliquot of sample is segregated from the remaining portion of the sample placed into the device. The term "aliquot" refers to a selected volume of sample. An aliquot need not be any particular volume but will be an amount of sample sufficient to perform an assay for the presence or amount of an analyte.

The term "valve assembly" refers to a component that regulates the flow of liquid by opening, shutting, or partially obstructing an aperture. The valve may be mobile itself, or may be an immobile component that is moved into a position to open, close, or partially obstruct the aperture by the relative movement of the cups or other parts of the device. In one embodiment the valve is a type of slide valve composed of an immobile component constructed of plastic, rubber, or another material. In various other embodiments the valve assembly can be a ball valve, mitral valve, butterfly valve, check valve, or another type of valve. Devices of the invention can have more than one valve and more than one reservoir.

In one embodiment the first cup is rotatably disposed within the second cup, where the first cup has first and second positions within the second cup. The valve assembly can be a valve member that seals the reservoir from liquid communication with the interior of the first cup when the first cup is located in the second position. In one embodiment the device also has a lid that contains at least one key element, and the first cup contains at least one engagement mechanism. The at least one key element is inserted into the at least one engagement mechanism when the lid is placed onto the first and second cups. The first cup has a first position where liquid communication occurs between the reservoir and the interior of the first cup, and a second position where the valve member seals the at least one reservoir from liquid communication with the interior of the first cup. In one embodiment the one or more test elements are lateral flow test elements, for example, test strips, which can produce a colorimetric signal when an analyte of interest is present.

In another embodiment the valve member is located on the second cup and can be placed in a first position where the aperture is open, and a second position where the aperture is closed. In one embodiment liquid communication does not occur between the reservoir and the test elements when the valve member is located in the first position, but liquid communication between the reservoir and the test elements does occur when the valve member is located in the second position. Thus, the passageway is closed when the first cup is in the first position, and open when the first cup is in the second position. The first and second positions can be conveniently located about 90 degrees radially apart. The lid can be rotatably sealable about the top of the second cup.

In one embodiment the device contains a seal that prevents liquid communication between the reservoir and the test element when the first cup is located in the first position. The seal can be a second valve or O-ring or another type of seal located at a base of the one or more sealable reservoirs. In one embodiment a seal is an O-ring situated at the base of the reservoir. The second valve or O-ring seals the reservoir to prevent liquid communication between the reservoir and the test elements when the first cup is in the first position. But when the first cup is moved into the second position, the seal provided by the valve or O-ring is broken, and liquid communication then occurs between the reservoir and the test elements. In other embodiments the seal can be a caulking, rubber seal, or other water impermeable material. In other embodiments liquid communication occurs between the reservoir and the one or more test elements, through the passageway, when the first cup is located in the second position. An "O-ring" is a gasket which seals the reservoir from liquid communication with the passageway. It is usually made of rubber or plastic, but any material able to fulfill the function of sealing the reservoir from liquid communication is suitable. The O-ring usually is in the form of a flat ring or loop, but may take any shape or form consistent with its function. The "passageway" is the space between the reservoir and the sample application zone of the test element, which space can take any form. In other embodiments no O-ring is used, but a second valve seals the reservoir from liquid communication with the test element when the first cup is in the first position, and allows liquid communication between the reservoir and test elements when the first cup is in the second position.

In another embodiment the invention can have an access opening. An "access opening" refers to an opening on the top or side of the device which can be opened without spilling the contents of the device, and which allows the operator to gain access to the sample within without the need to remove the top of the device. The access opening will typically take the form of an opening large enough for a pipette or other sampling device to be inserted to remove an aliquot of sample, but the opening can take any shape or size consistent with its function.

In another aspect the present invention provides methods of determining the presence or amount of an analyte in a sample. The methods involve placing the sample into a device of the present invention as described herein, placing the lid on the first and second cups and engaging the key elements in the engagement mechanisms; turning the lid so that the first cup is moved from the a first position to a second position, thereby sealing the aperture and preventing fluid flow from the interior of the first cup to the reservoir, and thereby breaking a seal at the reservoir and permitting fluid flow from the reservoir to the testing elements through the passageway; and determining the presence or amount of analyte in the sample. In embodiments using an O-ring or other type of seal, fluid flows from the reservoir due to breaking of the seal of the reservoir provided by the O-ring or other seal. In embodiments using a second valve, fluid flows from the reservoir by opening of the second valve.

In one embodiment the key elements are comprised on the underside of the lid. For example, the lid can contain a circular portion in the center bottom of the lid which contains the key elements that protrude from the circular portion. At least two key elements are desirably present, but four will result in a more stable turning mechanism. Of course six or any number of key elements can also be used. The lid can be rotatably sealable about the top of the first and second cups. The lid can fit over the top of the two cups together and form a seal. In one embodiment the O-ring is located at a base of the one or more reservoirs and seals the reservoir from liquid communication with the passageway when the first cup is in the first position. The O-ring seal is broken and opened when the first cup is turned to the second position, thereby allowing liquid communication between the reservoir and the test elements. The liquid communication occurs between the reservoir and the test elements through the passageway.

In another aspect the present invention provides kits including a device of the invention as described herein, and instructions for use of the device in the determination of the presence or amount of an analyte in a fluid sample.

The summary of the invention described above is not limiting and other features and advantages of the invention will be apparent from the following detailed description, as well as from the claims.

BRIEF DESCRIPTION OF THE DRAWINGS

FIG. 1A is a top orthogonal view of the lid or cap. FIG. 1B is a horizontal side orthogonal view. FIG. 1C is a vertical orthogonal view of another side. FIG. 1D is a sectional side view. FIG. 1E is an orthogonal view of the bottom of the device. FIG. 1F is a perspective view. In this embodiment, an elliptical O-ring is used to provide the barrier between the reservoir and the test elements.

FIG. 3 is a sectional perspective side view of the embodiment of FIG. 1 without the lid, showing elliptical component alignment between the bottoms of the two cups.

FIG. 4 is another cross sectional perspective side view including lid of the embodiment of FIG. 1, showing the first and second cups 90 degrees out of alignment (after rotation of the first cup). This Figure shows the elliptical O-ring used in this embodiment.

DETAILED DESCRIPTION

Among other aspects, the invention provides a new diagnostic device. The hardware of the device provides for collection of sample, an assay capability, as well as a preservation area for the preservation of an uncontaminated aliquot of sample in one area of the device. Thus, a portion of the collected sample is segregated so that it remains intact and unadulterated relative to the portion assayed. The device can be disposable or reusable and can be made out of a translucent water-resistant plastic or polymer such that the sample and assay results can be visualized or monitored from outside the device, for example, with the unaided eye. While the devices will normally be disposed of after use, in one embodiment the device utilizes modular components and chambers that are provided preassembled for use, and in another embodiment can be provided in reversible format such that disassembly is also convenient, and so that the assay component of the device can be readily cleaned, changed and/or the sample aliquot previously assayed removed to ready the device for a second assay or batch of assays of the same or different type. Test elements can be provided in a cartridge format providing for ease of replacement.

The invention allows assays to be conducted with easier maintenance of sample purity/minimization of sample adulteration, and facile sample storage for later use. The valve assembly of the device permits sample aliquot shunting toward the test element when the operator is prepared to conduct the assay. The device features simplistic manual operation of the valve assembly or assemblies to effect aliquot segregation and analysis while maintaining intact the balance of originally collected sample, which may be conveniently retained or stored thereafter for later testing.

The following discussion describes one embodiment of the invention. Witi reference to the present disclosure, the person of ordinary skill in the art will realize other embodiments within the scope of the present disclosure.

Figure 1A:
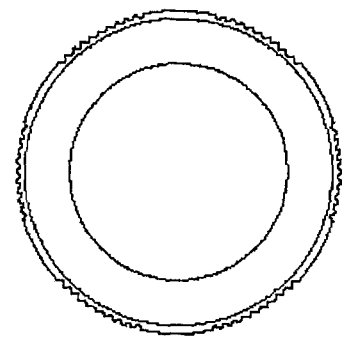
FIGS. 1A-F are various orthogonal and perspective views of one device embodiment of the invention.
Figure 1B:
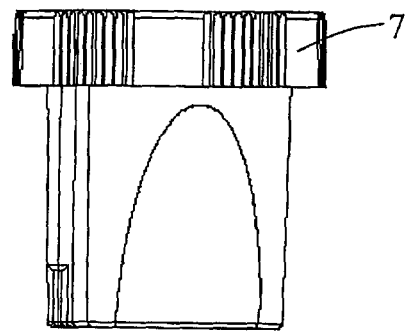
Figure 1C:
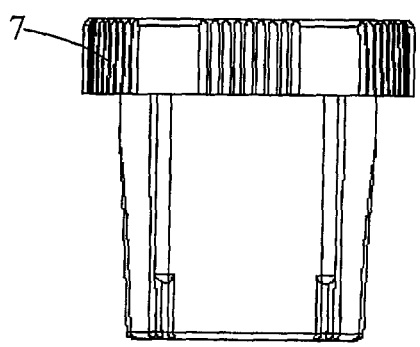
Figure 1D:
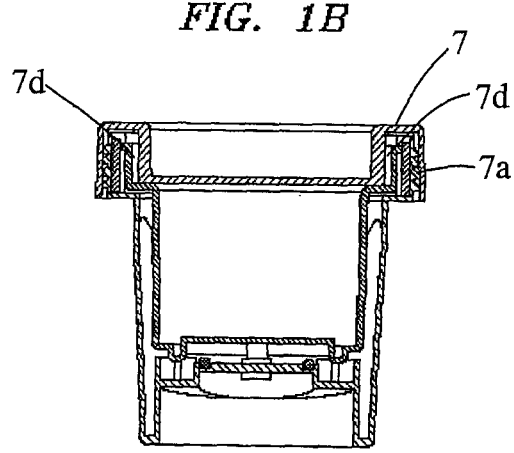
Figure 1E:
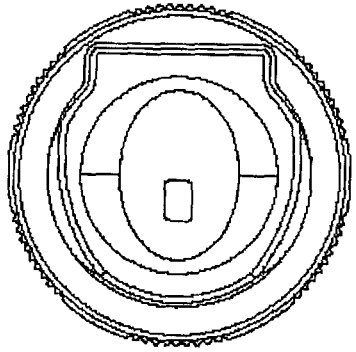
Figure 1F:
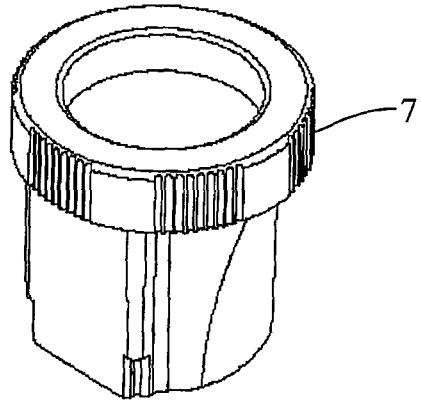
Figure 2:
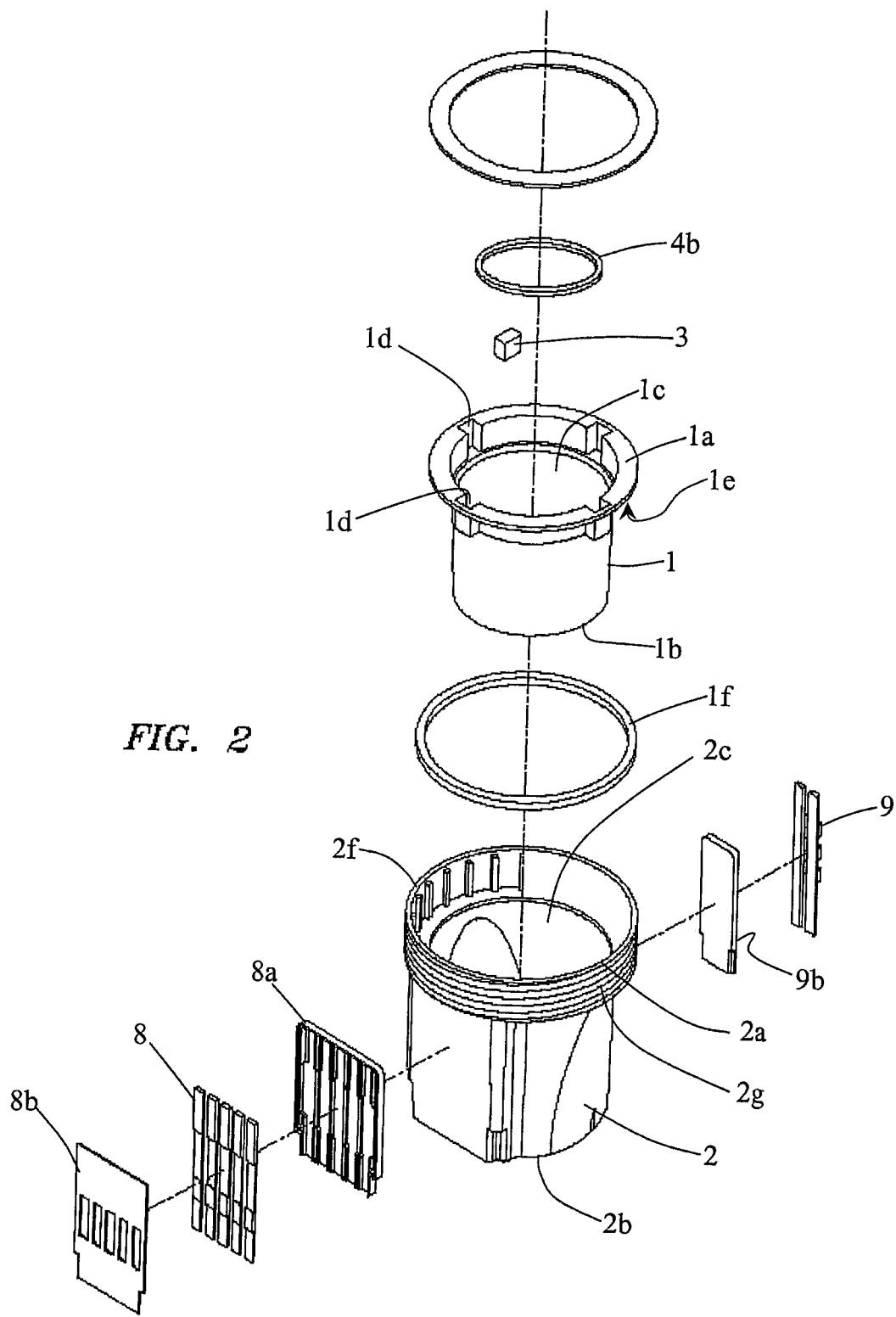
FIG. 2 is an exploded side view of the embodiment in FIG. 1.
Figure 5A:
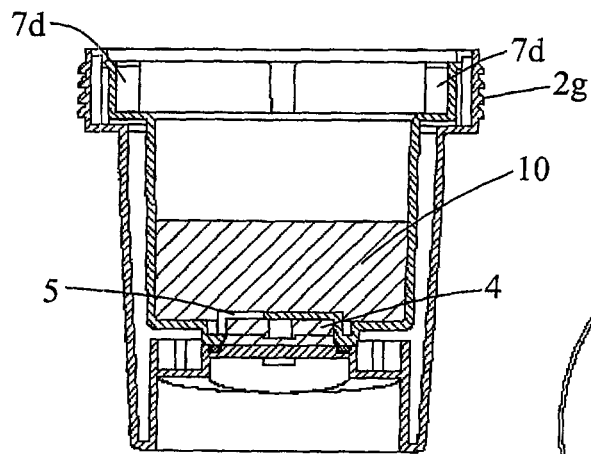
FIGS. 5A and B are, respectively, horizontal and vertical sectional views of the device embodiment of FIG. 1, showing the elliptical O-ring used in this embodiment aligned relative to one another, thereby allowing flow of fluid sample from the interior of the first cup to the reservoir.
Figure 5B:
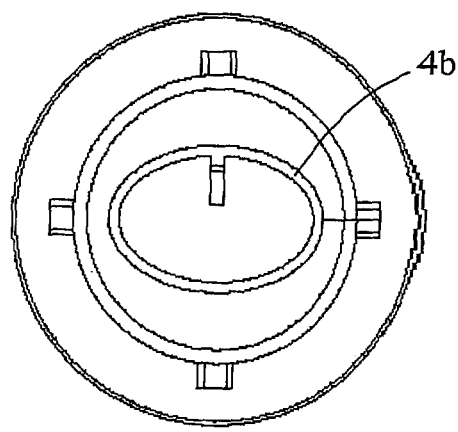
Figure 6A:
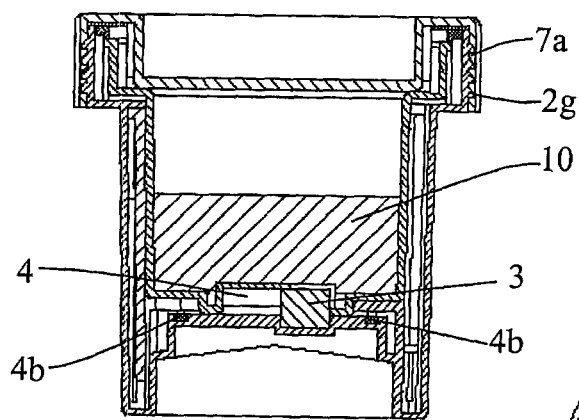
FIGS. 6A and 6B are, respectively, horizontal and vertical sectional views of the device embodiment of FIG. 1, showing the elliptical O-ring used in this embodiment offset by 90 degrees, thereby sealing the reservoir from fluid communication with the first cup, and allowing flow of fluid sample from the reservoir to the test elements.
Figure 6B:
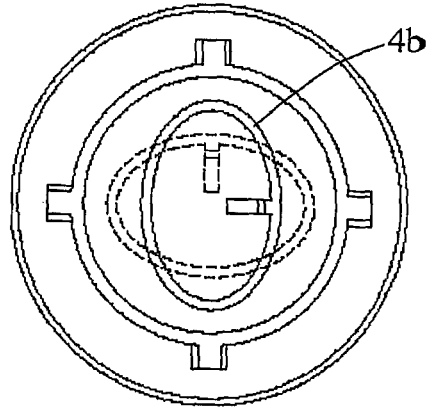

With reference to FIGS. 1-5, an inner cup 1 fits within an outer cup 2, the relative dimensions of each sufficiently compatible for the outer (second) cup to receive the inner (first cup) and for the inner cup to rotate within the outer cup. The cups each have a flanged rim (1a and 2a, respectively), bottom (1b and 2b, respectively), and side walls (1e and 2e, respectively). A valve assembly 3 interfaces with the reservoir 4 for regulating fluid communication of the sample between the interior of the cup 1 and the test elements 8, which in this embodiment are test strips. The test elements 8 can be located in a test element support 8a and provided with a cover 8b, which can indicate the analytes being tested for. Similarly, the device can be provided with adulterant indicators 9, which can also be present on an adulterant element support 9a. In this embodiment the valve assembly is a structure made of rubber that is positioned to allow fluid communication between the interior of the first cup and the reservoir when the first cup is in the first position. When the first cup is moved into the second position the valve structure will block the aperture 5 in the first cup, thereby blocking fluid communication between the interior of the first cup and the reservoir.

When the sample 10 is collected a portion of the sample flows into the reservoir 4 through an aperture 5 or slot in cup bottom 1b. In this embodiment the reservoir 4 is formed of a raised portion of cup bottom 1b providing the volume of the reservoir. This embodiment also uses an O-ring 4b as the seal at the base of the reservoir, preventing liquid communication between the reservoir 4 and the passageway and test elements. The O-ring is present in an elliptical groove in the inside bottom of the second cup 2b, thereby providing the seal (FIG. 3).

The bottom of cup 1b can also have a corresponding elliptical groove or ledge to assist in seating the O-ring. During sample collection, the elliptical components are all aligned, and the aperture 5 is open.

Following sample collection, the lid is applied and the key elements on the underside of the lid are engaged in the engagement mechanisms 1d. The key elements and engagement mechanisms will provide support for an applied force that rotates the inner cup 1 within the outer cup 2. The inside lip of the lid can have screw threads that are complementary to screw threads located on the outside rim 2g of the second cup 2. The lip of the first cup turns downward, and on the underside of the exterior rim 1a of the first cup 1 are retaining teeth 1e (not visible). On the periphery of the underside of the rim is a rubber gasket 1f. The retaining teeth 1e are designed to be received by recesses (not visible) in the outer cup rim 2a. Thus, the first cup fits over the rim of the second cup 2a, and the retaining teeth are engaged with the recesses present on the rim of the second cup. In this embodiment, the rubber gasket if is held in place by the retaining teeth. When the cups are mated, the retaining teeth fit into the recesses, and the rubber gasket seals the space between the rims of the two cups. When the first cup is seated into the second cup, the parts are mated so that the lip on the rim of the first cup covers the lip 2f on the rim of the second cup, and together provide a surface on which the lid may be screwed onto the two cups.

When lid 7 is placed onto the two cups (the cup within a cup), the key elements engage the engagement mechanisms. The screw threads on the inner lid 7a also engage the complementary screw threads on the outer rim of the second cup. Lid 7 is of suitable dimension to fit over each of the cup rims 1a and 2a, engaging each cup—the first cup through the key elements being placed within the engagement mechanisms, and the second cup through the complementary screw threads.

During use, inner lid threads 7a engage threads of the rim of the second cup 2g in screwtype fashion to effectively seal cups 1 and 2 from the exterior environment. Lid key elements 7d (two of four visible in FIG. 5A) simultaneously engage the engagement mechanisms Id on the rim of the inner cup. Thus, the lid is "locked" onto the cup within a cup. This allows the cups 1 and 2 to not only be sealed from the external environment, but also to be manipulated relative to one another to actuate the valve assembly 3 and thereby perform the assay.

When a force is applied to tighten the lid 7 onto the cup within a cup, the retaining teeth are dislodged from the recesses, thus causing the first cup to be turned within the second cup. This occurs under a normal turning force easily applied by hand. As the first cup turns within the second cup, the seal provided by the O-ring 4b is broken and the aliquot held in the reservoir 4 is shunted to a passageway 6. At the same time, the aperture 5 of the first cup is closed and sealed by the new (second) position of the valve assembly 3. Thus, the remaining contents of the first (inner) cup 1 are therefore sealed and can be used at a later time for confirmation testing.

Upon shunting, the sample portion in the reservoir 4 flows into the passageway 6. Lateral flow test elements 8 are affixed to the outer cup's side walls 2b or to another chamber in fluid communication with the passageway, and upon breaking of the O-ring seal are thereby placed in fluid communication with the sample in the passageway 6.

In another embodiment the lid 7 can contain a suitably dimensioned recesses on the underside of the lid to fit cup bottom 1b, either prior to placement of cup 1 within cup 2, or after concluding an assay and separating cup 1 from 2, e.g., in prelude to cleaning and/or the preparation and running of another assay or series of assays, e.g., in identical or alternatively configured outer cups harboring identical or different test elements 8a, b. Further, the lid outer side surface may be suitably textured so as to enhance the end-user's "grip" on the device. The individual components of the device are readily produced, e.g., by standard injection molding techniques and may assume a wide range of shapes, resiliencies and geometries so long as functionally compatible with one another in furtherance of the principles discussed above. Depending on the exact embodiment and configuration, the device may consist of one or more flexible or rigid components, depending on the specific material used. The device may be constructed of any suitable material such as, for example, pressed hardboard, metals, ceramics, plastics, and polymers. Suitable polymers include, but are not limited to, polycarbonate, polypropylene and cycloolifins.

Valve Assembly

The valve assembly functions by rotation of one cup relative to the other cup, such as by a lid having key elements that fit into engagement mechanisms on the first cup providing a location to apply the force to turn the first cup within the second. In one embodiment, the lid seals the top of the second cup so as to prevent sample from leaking out of the cups. In another embodiment, the valve assembly (or assemblies) can be driven by handles on the lateral exterior of the outer cup, such that turning the handle shunts an aliquot sample into another chamber where it may then be tested using a test element or component as described above. In still other embodiments, one or more valve assemblies may be electrically operated and responsive to an external electric impulse routed to the valve assembly.

The valve can be a rubber or plastic tab situated at the bottom of the inside of the second cup, so that it will be positioned in the reservoir when the first cup is placed into the second cup. Because it is rigid and water impermeable, it can be positioned such that when the first cup is rotated within the second cup, the valve will be moved into position to block the aperture present in the first cup, thereby preventing fluid communication between the interior of the first cup and the reservoir.

Samples, Sample Aliquots, and Sample Analytes

Some embodiments of the device utilize one or more key elements for manipulating the valve assembly (or assemblies). The key elements engage the engagement mechanisms, which in one embodiment are located on the top inside rim of the first cup, and provide a location for applying force to rotate the first cup within the second cup. In some embodiments the key element is integral to the lid, which fits over and rotatably engages the engagement mechanisms on the inside rim of the first cup, such that (a) the valve assembly is moved into position to block the aperture and prevent fluid communication between the interior of the first cup and the reservoir.

In various embodiments one or more gaskets may be used to prevent leaking between the different parts of the device. These gaskets can take the form of O-rings, seals of water impermeable materials, etc.

A "sample" is any material to be tested for the presence or amount of an analyte. Examples of liquid samples that may be tested using a test device of the present invention include bodily fluids such as urine, blood, serum, plasma, saliva, sputum, sweat, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semisolid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution such as a buffer, diluent, extraction buffer, or reagent. The sample can be macerated, frozen and thawed, or otherwise extracted to form a fluid sample. Residual particulates can be removed or reduced using conventional methods, such as filtration or centrifugation. By "sample aliquot" is meant a portion of the sample that undergoes testing by the test element.

An "analyte" is a compound or composition of interest within the sample that is to be detected and/or measured by the test element. Any analyte can be detected using the present invention for which there is a suitable test element. In one embodiment the analyte sought to be detected is a drug of abuse. A "drug of abuse" (DOA) is a drug that is taken for non-medicinal reasons (usually for mind-altering effects). The abuse of such drugs can lead to physical and mental damage and (with some substances) dependence, addiction and/or death. Examples of DOAs include cocaine; amphetamines (e.g., black beauties, white bennies, dextroamphetamines, dexies, beans); methamphetamines (crank, meth, crystal, speed); barbiturates (Valium, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone). But any analyte can be detected using the invention.

An analyte can also relate to measuring or determining the adulteration of a sample, such as by dilution or other tampering, e.g., supplying a sample from another species, subject or nonhuman source, or by adding an agent that can alter the composition of a sample and defeat the purpose of the assay. Such adulteration analytes can be chosen based on the particular application and sample type being analyzed, and the sources or types of possible adulteration. Such analytes are optionally referred to herein as adulteration analytes or adulteration indicators.

Analytes can also be specific binding molecules, such as antibodies or derivatives or fragments or active fragments thereof. Specific binding molecules bind to another molecule or complex with greater affinity or avidity relative to other sample or analyte compounds. The antibody can be monoclonal or polyclonal and can be prepared by techniques that are well known in the art such as, for example, immunization of a host and collection of sera or hybrid cell line, e.g., hybridoma, technology.

Test Elements

A "test element" is the component containing the reagents that form the basis of the assay, and provides a detectable signal when an analyte is present in a fluid sample. In one embodiment the test element is a test strip (e.g., a lateral flow test strip). In other embodiments the test element can be a slide, or a bibulous paper (e.g., filter paper) with a reagent applied thereon. Test elements typically contain one or more reagents that bind and/or react with one or more analytes of interest in a sample. Many different test elements and assays are commercially available that can be used in the devices and methods of the invention.

When the test element is a test strip, it may be made of bibulous or non-bibulous material. A test strip can include more than one material, which are then in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and mayor may not partially overlap one another. The material or materials of the test strip can be bound to a support or solid surface such as a supporting sheet of plastic, to increase its handling strength.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the lest strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

The zones can be arranged as follows: sample application zone, one or more reagent zones, one or more test results determination zones, one or more control zones, one or more adulteration zones, and fluid absorbing zone. If the test results determination zone includes a control zone, preferably it follows the analyte detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such a joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication. In addition to these embodiments of test strips, many other embodiments can be made.

It is also useful to provide test elements indicating the presence of adulteration contaminants. For example, an adulteration element can be included indicating the specific gravity of the urine sample, so that adulterants that would change the specific gravity of the urine will be detected. It is a common technique among those who would seek to defeat the results of an assay for drugs of abuse to add glutaraldehyde and other chemicals, and many other contaminants to a urine sample. Further, it is useful to include a test element for the physical parameter of temperature. If the sample provided is not of a normal temperature expected, it may provide an indication that the sample was carried to the test site and does not originate with the test subject. Many adulterants can be added to urine to defeat the purpose of drug screening, and as many test elements as thought desirable can be incorporated into the device. These adulterants and corresponding test elements are known in the art.

When a test strip includes an adulteration control zone, the adulteration control zone can be placed before or after the results determination zone. When a control zone is present in the results determination zone on such a test strip, then the adulteration control zone is preferably before the control zone, but that need not be the case. In the embodiment of the present invention where a test strip is a control test strip for the determination of an adulteration analyte and/or a control, then the adulteration control zone can be placed before or after the control zone, but is preferably before the control zone.

Samples that can be tested with the device of the present invention include liquids of biological origin (e.g., casing fluids and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. A preferred biological sample is urine. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other casing of water, effluent samples, soil samples, ground water, ocean water, and runoff water. Sewage and related wastes can also be included as environmental samples.

Any analyte can be tested for utilizing the present invention and a suitable test element. In particular, the present invention can be utilized for the detection of a drug of abuse in oral fluid. A "drug of abuse" (DOA) is a drug that is taken for non-medicinal reasons (usually for mind-altering effects). The abuse of such drugs can lead to physical and mental damage and (with some substances) dependence, addiction and/or death. Examples of DO As include cocaine; amphetamines (e.g., black beauties, white bennies, dextroamphetamines, dexies, beans); methamphetamines (crank, meth, crystal, speed); barbiturates (Valium©, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (POP); tetrahydrocannabinol (THC, pot, dope, hash, weed, etc.); and opiates (e.g., morphine, opium, codeine, heroin, oxycodone).

For example, analytes that can be tested using the present invention include but are not limited to creatinine, bilirubin, nitrite, protein (nonspecific), hormones (e.g. human chorionic gonadotropin, luteinizing hormone, follicle stimulating hormone, etc.), blood, leukocytes, sugar, heavy metals or toxins, bacterial components (e.g. proteins or sugars specific to a particular type of bacteria, such as *E. coli* 0157:H7, *S. aureus, Salmonella, C. perfringens, Campylobacter, L. monocytogenes, V parahaemolyticus,* or *B. cereus*) and physical characteristics of the urine sample, such as pH and specific gravity. Any other clinical urine chemistry analyte that can be adapted to a lateral flow test format may also be incorporated into the present device.

Example 1

A Sample Collection Container with Activatable Integrated Test Element

The devices of the invention can be utilized in a variety of contexts, for example, for pre-employment drug screening. The person to be tested provides a sample of urine in the inner (first) cup. In embodiments for pre-employment drug screening the device contains test strips for several common drugs of abuse, in this embodiment cocaine, methamphetamine, phencyclidine, THC, morphine, and amphetamines. These test strips utilize a competitive immunoassay format where labeled specific binding molecules (antibodies in this embodiment) for each drug being tested are present on the label zone of the test strip. The test lines contain the antigen being tested for. If analyte is present in the sample it is bound by labeled specific binding molecules in the label zone, thereby preventing the labeled antibody from binding to the test line. Thus, no signal occurs on the test line when analyte is present. Conversely, when no antigen is present in the saliva, the labeled antibodies bind to the test line providing the signal on the test line.

The test subject receives a device and provides a urine sample in the device. By the time the technician receives the device filled with urine sample, the reservoir will already have filled with urine sample. After receiving the device with the urine sample, the testing technician applies the lid, and engages the key elements in the engagement mechanisms. The retaining teeth of the first cup were previously seated in the recesses on the lip of the second cup. When the testing technician is prepared to begin the assay, the lid is screwed onto the device. This dislodges the retaining teeth from the recesses as the first cup turns within the second cup. When the technician rotates the first cup within the second cup, the valve assembly is moved into position to block the aperture in the first cup, thereby stopping fluid communication between the interior of the first cup and the reservoir. Also, as the first cup is rotated within the second cup, the seal located at the base of the reservoir is broken, and fluid communication occurs between the reservoir and the passageway, and finally the test strips.

Within about 30 seconds, the urine has flowed through the test strip and the control indication are present, signaling that the assay is complete. The technician then reads the results of the assay. If a positive result is found for any analyte, the device can be retained for a confirmatory test on the remaining sample, which is safely sealed and sequestered in the interior of the first cup.

The foregoing Example is not limiting of the invention and is merely representative of various aspects and embodiments. All documents cited are indicative of the levels of skill in the art to which the invention pertains, although none is admitted to be prior art. One skilled in the art will readily appreciate that the present invention is well adapted to carry out the objects and obtain the ends and advantages mentioned, as well as those inherent therein. The Example merely describes one embodiment, is exemplary, and is in no way intended as a limitation on the full scope of the invention. Certain modifications and other uses will occur to those skilled in the art, and are encompassed within the spirit of the invention as defined by the scope of the claims.

The reagents and test elements described herein are either commercially available or else readily producible without undue experimentation using routine procedures known to those of ordinary skill in the art, or else described in the documentation cited herein. For ex ample, illustrative test elements usable in the devices of the invention are available, e.g., from Acon Laboratories (San Diego, Calif., USA) as per http://www.aconlabs.com/products.html.

The invention illustratively described herein suitably may be practiced in the absence of any element or elements, limitation or limitations which is not specifically disclosed herein. Thus, for example, in each instance herein any of the terms "comprising", "consisting essentially of and "consisting of" may be replaced with either of the other two terms, endowing a different meaning under the patent laws.

The terms and expressions which have been employed are used as terms description and not of limitation, and there is no intention in the use of such terms anc expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group, and exclusions of individual members as appropriate. Other embodiments are apparent from the following claims.

The invention claimed is:

1. A device for determining the presence or amount of an analyte in a sample, comprising:
   a first cup comprising an interior for holding a liquid sample, a top, one or more sidewalls, and a bottom;
   a second cup having a top, one or more sidewalls, and a bottom, the first cup being disposed within the second cup;
   at least one reservoir for containing an aliquot of sample located between the first and second cups, the first cup further comprising an aperture venting from the interior of the first cup into an opening in the at least one reservoir;
   a valve assembly interfacing with the at least one reservoir for regulating liquid communication of the aliquot of sample from the interior of the first cup to the at least one reservoir via the aperture;
   one or more test elements comprising a sample application zone, for determining the presence or amount of an analyte in the liquid sample; and
   a passageway connecting the at least one reservoir and the sample application zone;
   wherein the first cup has a first position in which the valve assembly allows liquid communication between the interior of the first cup and the at least one reservoir via the aperture being radially aligned with the opening, and a second position in which the valve assembly seals the at least one reservoir from liquid communication with the interior of the first cup, the aperture and the opening being radially unaligned, and wherein upon rotation of the first cup within the second cup, the first cup transitions from the first position to the second position and the valve assembly provides liquid communication between the at least one reservoir and the one or more test elements via the passageway.

2. The device of claim 1 further comprising a lid that comprises at least one key element, and wherein the first cup comprises at least one key hole.

3. The device of claim 2 wherein the at least one key element is inserted into the at least one key hole when the lid is placed onto the first and second cups.

4. The device of claim 2 wherein the lid is rotatably sealable about the top of the second cup.

5. The device of claim 1 wherein the one or more test elements are lateral flow detection components.

6. The device of claim 5 wherein the one or more test elements are test strips.

7. The device of claim 6 wherein the one or more test strips produce a colorimetric signal when an analyte of interest is present.

8. The device of claim 1 wherein the valve assembly is comprised on the bottom of the second cup.

9. The device of claim 1 wherein the first and second positions are located about 90 degrees radially apart.

10. The device of claim 1 further comprising a seal located at a base of the at least one reservoir.

11. The device of claim 10 wherein the seal is an O-ring, which seals the at least one reservoir to prevent liquid communication between the at least one reservoir and the one or more test elements when the first cup is in the second first position.

12. The device of claim 1 further comprising an access opening.

13. A method of determining the presence or amount of an analyte in a sample comprising:
    placing the sample into a device, the device comprising:
    a first cup comprising an interior for holding a liquid sample, a top, one or more sidewalls, a bottom, and one or more engagement mechanisms;
    a second cup having a top, one or more sidewalls, and a bottom, the first cup being disposed within the second cup;
    at least one reservoir for containing an aliquot of sample located between the first and second cups, the first cup comprising an aperture venting from the interior of the first cup into the at least one reservoir;
    a valve assembly interfacing with the at least one reservoir having an opening therein for regulating liquid communication of the aliquot of sample from the interior of the first cup to the at least one reservoir via alignment of the aperture with the opening of the at least one reservoir;
    one or more test elements for determining the presence or amount of an analyte in the liquid sample;
    a passageway between the at least one reservoir and the one or more test elements;
    a lid comprising one or more key elements which engage the one or more engagement mechanisms, wherein the first cup has a first position in which the valve assembly allows liquid communication between the interior of the first cup and the at least one reservoir via the aperture being radially aligned with the opening, and a second position in which the valve member seals the at least one reservoir from liquid communication with the interior of the first cup, the aperture and the opening being radially unaligned, and wherein upon rotation of the first cup within the second cup, the first cup transitions from the first position to the second position and the valve assembly provides liquid communication between the at least one reservoir and the one or more test elements via the passageway;
    placing the lid on the first and second cups and engaging the one or more key elements with the one or more engagement mechanisms;
    turning the lid to rotate the first cup from the first position to the second position; and
    determining the presence or amount of analyte in the sample.

14. The method of claim 13 wherein the one or more key elements are comprised on an inside lip of the lid.

15. The method of claim 13 wherein the one or more test elements are lateral flow detection components.

16. The method of claim 15 wherein the one or more detection components are test strips.

17. The method of claim 16 wherein the one or more test strips produce a colorimetric signal when an analyte of interest is present.

18. The method of claim 13 wherein the first and second positions are located about 90 degrees radially apart.

19. The method of claim 18 wherein the lid is rotatably sealable about the top of the first and second cups.

20. The method of claim 13, wherein the device further comprises a seal located at a base of the at least one reservoir.

21. The method of claim 20 wherein the seal is broken when the first cup is turned to the second position.

22. A kit comprising:
    a) the device of claim 1; and
    b) instructions for use of the device.

* * * * *